United States Patent
Poirier et al.

(10) Patent No.: US 9,664,668 B2
(45) Date of Patent: May 30, 2017

(54) WHOLE BLOOD ANALYTIC DEVICE AND METHOD THEREFOR

(75) Inventors: Michael Poirier, Vista, CA (US); John Stephen Middleton, Carlsbad, CA (US); Suzanne Marie Poirier, Vista, CA (US)

(73) Assignee: QUALIGEN, INC., Carlsbad, CA (US)

( * ) Notice: Subject to any disclaimer, the term of this patent is extended or adjusted under 35 U.S.C. 154(b) by 129 days.

(21) Appl. No.: 14/398,409

(22) PCT Filed: May 3, 2012

(86) PCT No.: PCT/US2012/036248
§ 371 (c)(1),
(2), (4) Date: Oct. 31, 2014

(87) PCT Pub. No.: WO2013/165420
PCT Pub. Date: Nov. 7, 2013

(65) Prior Publication Data
US 2015/0086970 A1    Mar. 26, 2015

(51) Int. Cl.
G01N 21/75 (2006.01)
G01N 33/49 (2006.01)
G01N 1/40 (2006.01)
B01D 69/02 (2006.01)

(52) U.S. Cl.
CPC ......... G01N 33/491 (2013.01); G01N 1/4005 (2013.01); *B01D 69/02* (2013.01); *B01D 2319/06* (2013.01); *B01D 2325/36* (2013.01); *B01D 2325/38* (2013.01)

(58) Field of Classification Search
CPC ............... G01N 33/491; G01N 1/4005; B01D 2319/06; B01D 2325/38; B01D 2325/36; B01D 69/02
See application file for complete search history.

(56) References Cited

U.S. PATENT DOCUMENTS

| | | |
|---|---|---|
| 3,092,465 A | 6/1963 | Adams, Jr. |
| 3,630,957 A | 12/1971 | Rey |
| 3,663,374 A | 5/1972 | Moyer |
| 4,246,107 A | 1/1981 | Takenaka |
| 4,256,693 A | 3/1981 | Kondo |
| 4,477,575 A | 10/1984 | Vogel et al. |
| 4,753,776 A | 6/1988 | Hillman |
| 4,987,085 A | 1/1991 | Allen |
| 5,064,541 A | 11/1991 | Jeng |
| 5,435,970 A | 7/1995 | Mamenta et al. |

(Continued)

FOREIGN PATENT DOCUMENTS

| | | |
|---|---|---|
| JP | 2011504592 T | 2/2011 |
| JP | 4885134 B2 | 2/2012 |

(Continued)

*Primary Examiner* — Dennis M White
(74) *Attorney, Agent, or Firm* — Fish & Tsang LLP

(57) ABSTRACT

Devices and methods are presented in which a plasma separation device with a first and second portion separates a blood containing fluid. Most preferably, the first portion produces a cell fraction and a plasma fraction, and the second portion captures the plasma fraction. A first actuator then fluidly isolates a portion of the plasma fraction within the second portion, and a second actuator moves the isolated portion of the plasma fraction from the second portion.

20 Claims, 1 Drawing Sheet

(56) References Cited

U.S. PATENT DOCUMENTS

| | | |
|---|---|---|
| 6,291,249 B1 | 9/2001 | Mahant |
| 6,300,138 B1 | 10/2001 | Gleason |
| 6,426,230 B1 | 7/2002 | Feistel |
| 6,821,790 B2 | 11/2004 | Mahant |
| 7,094,354 B2 | 8/2006 | Pugia |
| 7,214,544 B2 | 5/2007 | Poirier |
| 7,615,191 B2 | 11/2009 | Buechler |
| 7,629,165 B2 | 12/2009 | Wyatt |
| 7,754,499 B2 | 7/2010 | Poirier |
| 7,871,813 B2 | 1/2011 | Wyatt |
| 2004/0129678 A1 | 7/2004 | Crowley |
| 2004/0229347 A1 | 11/2004 | Perez |
| 2007/0134810 A1* | 6/2007 | Yang ............... G01N 33/54366 436/514 |
| 2011/0041591 A1 | 2/2011 | Gupta |
| 2012/0024788 A1 | 2/2012 | Kelso |

FOREIGN PATENT DOCUMENTS

| | | |
|---|---|---|
| WO | 2010112934 A1 | 10/2010 |
| WO | 2011035385 A1 | 3/2011 |
| WO | 2012015926 A2 | 2/2012 |

* cited by examiner

WHOLE BLOOD ANALYTIC DEVICE AND METHOD THEREFOR

FIELD OF THE INVENTION

The field of the invention is analytical devices, and especially as it relates to devices that include a whole blood separation unit.

BACKGROUND OF THE INVENTION

In vitro diagnostic tests to identify and treat diseases have become common tools in hospitals, homes and physician's offices. Biological fluids such as blood, urine or cerebrospinal fluids, which may at times contain blood, are the most frequently employed biological samples for such tests. Of these, blood is the most commonly used. However, for most testing applications, blood must be separated into plasma or serum prior to testing.

Blood separation technologies can generally be grouped within three categories—centrifugation, filtration, and solid-phase separation.

Centrifugation is generally used to separate cellular components from serum or plasma because (1) centrifugation can separate cellular components from serum or plasma at an efficiency of greater than 95%; (2) centrifuges do no require highly trained personnel to operate; and (3) centrifugation allows concurrent processing of multiple samples in a relatively short time. However, some difficulties exist with centrifugation. For example, centrifuges are expensive, require the need for multiple steps (e.g., aliquoting through the use of precision pipette which can vary depending upon the technique of the operator), and are often unavailable at points of care such as a home, school, or bedside.

Filtration techniques to separate components of blood can be performed in a variety of manners. U.S. Pat. No. 4,987,085 to Allen et al., for example, describes a filtering system with descending pore size using a combination of glass fiber membranes and cellulose membranes. U.S. Pat. No. 4,753,776 to Hillman et al. discloses a glass microfiber filter using capillary force to retard the flow of cells. U.S. Pat. No. 4,256,693 to Kondo et al. discloses a multilayered chemical analysis element with filter layers made from at least one component selected from paper, nonwoven fabric, sheet-like filter material composed of powders or fibers such as man-made fibers or glass fibers. U.S. Pat. Nos. 3,663,374 and 4,246,693 disclose membrane filters for separating plasma from whole blood and U.S. Pat. Nos. 3,092,465, 3,630,957, 3,663,374, 4,256,693, 4,246,107, 4,330,410 disclose further filtration systems, some of which make use of small-pore membranes.

In general, filtration can be favorable because filtration reduces the volume of blood required to only a few drops. However, significant amounts of plasma may be retained and lost in the filters of known devices, and low concentrations of analytes derived from small volumes of blood are difficult to detect.

Solid-phase separation involves a surface having the ability to bind to a target. In other words, the surface effectively acts to immobilize and remove the target from the sample.

One type of solid-phase separation is magnetic separation, in which a target is captured by magnetically attractable beads. U.S. Pat. No. 7,214,544 to Poirier et al. describes an apparatus and method of blood separation using magnetic beads that are coupled to an affinity marker wherein the target is separated from the rest of the fluid using magnetic force and an automatic mechanical force. Furthermore, U.S. Pat. No. 6,291,249 to Mahant et al. describes the use of antibodies that are coupled to the surfaces of paramagnetic beads. One advantage of using magnetic separation is the absence of physical barriers which tends to make the separation relatively gentle. However, a major limitation with applying known magnetic separation is that multiple anti-ligands are required to remove all of the various types of cells and sub-cellular particles. Moreover, lack or absence of ligands on the cells due to pathological conditions, genetic diseases or genetic variations or life cycles of cells generally reduce the efficiency with which the anti-ligands bind with the target cells.

Thus, there is still a need to provide improved methods and apparatus for separating blood into its constituent parts, and especially for separating plasma or serum from whole blood.

SUMMARY OF THE INVENTION

The present invention is directed to devices and methods for sample manipulation and tests using whole blood in a device having a plasma separation device. Most typically, the plasma separation device has a first and second portion to separate a blood containing fluid, wherein the first portion produces a cell fraction and a plasma fraction, and wherein the second portion captures the plasma fraction. A first actuator is then used to fluidly isolate a portion of the plasma fraction within the second portion, while a second actuator is used to move the isolated portion of the plasma fraction from the second portion.

In one preferred aspect of the inventive subject matter, an analytic device has a sample receiving compartment, and further includes a plasma separation device that is at least partially disposed in the sample receiving compartment. Most typically, the plasma separation device comprises a first portion that separates blood into a cell fraction and a plasma fraction, and a second portion that captures at least a portion of the plasma fraction. It is further contemplated that the analytic device has a first area that, when compressed by a first actuator, restricts flow of the plasma fraction between the first and the second portion, and has a second area that, when compressed by a second actuator, causes flow of a metered volume of the plasma fraction into at least one of the sample receiving compartment and a second compartment.

In particularly preferred embodiments, the first portion is or comprises a hydrophobic separation membrane, while the second portion is or comprises a hydrophilic membrane that has a void volume for collection of a predetermined volume of plasma. Most typically, the first and second portions are fluidly coupled to each other to allow capillary flow of the plasma fraction from the first portion to the second portion. While not limiting to the inventive subject matter, it is generally preferred that the first and/or second area is formed from a flexible wall of the analytic device, and that the first actuator is configured as a knife edge. The metered volume is then determined by movement of a second actuator and/or the void volume in a membrane in the second portion of the plasma separation device. Additionally, it is contemplated that the devices presented herein will include a third compartment that comprises a reagent, and that is fluidly coupled to the sample receiving compartment to allow flow of the reagent into the second portion. In yet further suitable devices, a dried and dissolvable indicator reagent may be included in the first and/or second portion in an amount effective to produce a visible indicator in the second portion when a satisfactory amount of the plasma fraction has been collected in the second portion.

Therefore, and viewed from a different perspective, the inventor also contemplates a method of manipulating a sample for a diagnostic test using devices as described herein. Most preferably, contemplated methods will include a step of contacting a plasma separation device with a blood-containing fluid, wherein the plasma separation device has a first portion and a second portion. In another step, the first portion is used to separate the blood-containing fluid into a cell fraction and a plasma fraction, and the second portion is used to capture the plasma fraction. A first actuator is then employed to fluidly isolate a portion of the plasma fraction within the second portion, and a second actuator is used to move the isolated portion of the plasma fraction from the second portion.

In especially preferred aspects, the plasma separation device is at least partially disposed within a container, and/or separation of the blood-containing fluid is driven by capillary action. As noted before, it is generally preferred that first actuator has a knife edge that compresses part of the second portion of the plasma separation device, and/or that the second actuator compresses the second portion to thereby move the isolated portion of the plasma fraction. It is also contemplated that suitable methods will include a step of reacting a component in the plasma fraction with a reagent while the plasma fraction is in the second portion, and that the plasma fraction and the reagent are moved from the second portion using the second actuator.

Thus, and viewed from yet another perspective, the inventor also contemplates a method of manipulating a sample for a diagnostic test that includes a step of using capillary force in a plasma separation device to separate a blood-containing fluid into a cell fraction and a plasma fraction. In another step, at least some of the plasma fraction is received and retained in a compressible membrane, and a first portion of the compressible membrane is compressed to thereby fluidly isolate a portion of the plasma fraction within the compressible membrane. In a further step, a second portion of the compressible membrane is compressed while maintaining compression of the first portion to thereby dispense a predetermined volume of the plasma fraction from the compressible membrane.

Most typically, the compressible membrane is coupled to a hydrophobic separation membrane. As noted above, it is generally preferred that at least one of the steps of compressing the first and the second portion is performed through a flexible wall of a container. In still further preferred methods, a step of reacting a component in the plasma fraction with a reagent is included while the plasma fraction is in the second portion.

Various objects, features, aspects and advantages of the inventive subject matter will become more apparent from the following detailed description of preferred embodiments, along with the accompanying drawing figures in which like numerals represent like components.

DETAILED DESCRIPTION

The inventor has discovered that fluid management of various biological fluids, and especially blood-containing fluids can be simplified by use of an analytic device with a plasma separation device that is coupled to or comprises a portion that receives and retains at least some of the plasma fraction in a compressible membrane. Compression of a first portion of the compressible membrane will fluidly isolate a portion of the plasma fraction within the compressible membrane, and compression of a second portion of the compressible membrane while maintaining compression of the first portion will dispense a predetermined volume of the plasma fraction from the compressible membrane.

Figure 1A:
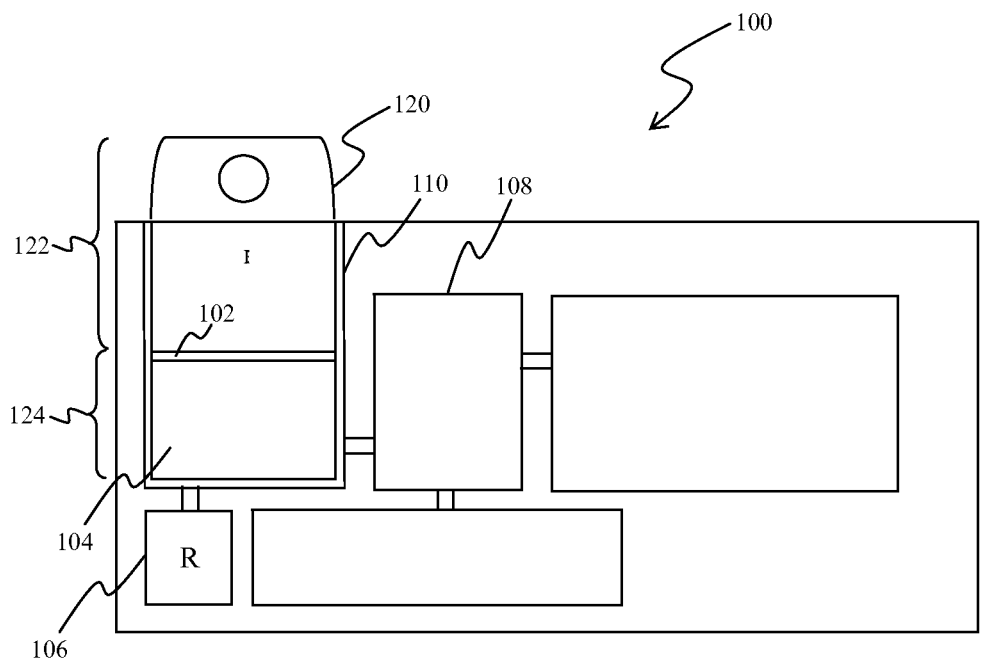
FIG. 1A is an exemplary schematic illustration of an analytic device with a plasma separation device according to the inventive subject matter.

FIG. 1A schematically illustrates an exemplary analytic device 100 according to the inventive subject matter have a sample receiving compartment 110 and a plasma separation device 120 that is at least partially disposed in the sample receiving compartment. The plasma separation device 120 is composed of two portions, the first 122 which is configured to separate blood into a cell fraction and a plasma fraction, and the second 124, which is configured to capture a portion of the plasma fraction. Moreover, the analytic device 100 has a first area 102 that, when compressed by an actuator, restricts the flow of the plasma fraction between the first 122 and the second portion 124. Furthermore, the analytic device has a second area 104 that, when compressed by an actuator, causes a flow of a metered volume of the plasma fraction into at least one of a second compartment 106 and third compartment 108. In a further embodiment, the second compartment 106 may contain a reagent (R), wherein the reagent may be introduced to plasma fraction located in the second area 104, and the mixture of the reagent and the sample are then compressed by an actuator (not shown) into a third compartment 108.

Figure 1B:
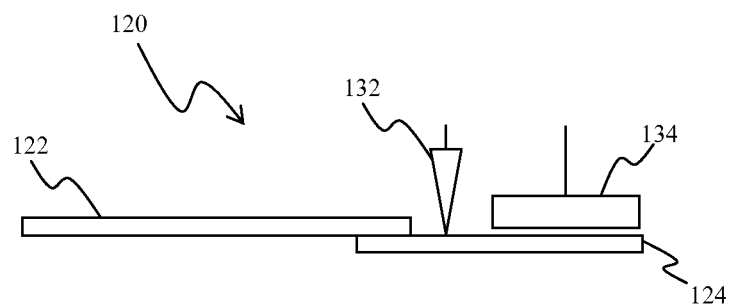
FIG. 1B is an exemplary schematic detail view of a plasma separation device and two compression actuators according to the inventive subject matter.

FIG. 1B schematically illustrates a detail view of an exemplary plasma separation device 120 according to the inventive subject matter depicting a plasma separation device and two compression actuators. The first portion 122 of the plasma separation device is configured to receive blood-containing fluid and to separate the fluid into a cell fraction and a plasma fraction. The second portion 124 of the plasma separation device is configured to capture a portion of the plasma fraction received from the first portion 122. A first compressive actuator 132 is used to restrict the flow between the first 122 and second 124 portion of the plasma separation device. Thereafter, a second compressive actuator 134 causes a flow of the metered volume of the plasma fraction from the second portion into the sample receiving compartment or other compartment (not shown). Further, the wall portions of the analytic device are not shown in this illustration.

Therefore, and in a more general sense, contemplated analytic devices are capable of receiving a sample where the sample is introduced to a plasma separation device. The plasma separation device may be partially disposed in the sample receiving compartment. Preferably, the plasma separation device is composed of: (1) a first portion which is configured to separate blood into a cell fraction and a plasma fraction, and (2) a second portion which is configured to capture at least a portion of the plasma fraction from the first portion. So isolated plasma fraction can then be reacted in, and/or moved from the plasma separation device in various manners. Most preferably, a defined volume of plasma fraction is isolated in the plasma separation device using mechanical pressure. To that end, contemplated analytic devices comprise areas which allow for control of the flow of the sample, sample components, and/or reagents. For example, a first area can be located in the second portion of the plasma separation device where when the first area is compressed by an actuator, the flow of the plasma fraction between the first and second portion is restricted. Provided that the first area is still compressed, a second area can be in the second portion where when the second area is compressed by an actuator, a metered volume of the plasma fraction flows into at least one of the sample receiving compartment and a second compartment.

The contemplated analytic devices may be composed of a flexible pouch with a multitude of chambers. The multitude of chambers may comprise of a sample receiving compartment, a plasma separation device, chambers for a cell fraction and a plasma fraction, different reagent chambers, mixing chambers, and waste chambers. A benefit of having a multitude of chambers is that contemplated analytical devices can perform a wide range of functions on a single analytical device. However, this benefit does not limit the option of having a plurality of contemplated analytical devices attached to one another. Having a plurality of contemplated devices allows a user to design each contemplated analytical device for a different test or the same test(s) for confirmation or a combination thereof. By having a flexible pouch, the analytic device is capable of bending without breaking. Nevertheless, the test pouch can also be rigid or a combination of rigid and flexible components so long as some degree of bending is allowed to withstand the force of a compressive actuator. Finally, contemplated analytic devices can be reusable or non-reusable.

Generally, a sample receiving compartment allows the analytic device to receive a plurality of samples. Contemplated samples to be received comprise of at least some blood in its composition. Moreover, the sample receiving compartment can be fluidly coupled to the plasma separation device to allow a blood-containing fluid to make contact with the plasma separation device. However, it is generally preferred that the plasma separation device is at least partially disposed on the sample receiving compartment and that the plasma separation device directly receives the blood-containing fluid. Thus, it may also be possible that the sample receiving device may be fluidly coupled to various compartments that are fluidly coupled to the plasma separation device. For example, U.S. Pat. No. 7,214,544 to Poirier et al. describes a configuration wherein a fluid receiving port is fluidly coupled to compartments, which are fluidly coupled to a separation chamber. In another embodiment, the sample receiving compartment and the plasma separation device may be a single piece. With respect to contemplated analytical devices, the sample receiving compartment may be located outside contemplated analytic devices. Alternatively, the sample receiving compartment may also be located inside contemplated analytical devices wherein a portion of the analytic device is exposed to allow for a sample to be received by the sample receiving compartment. This may be performed in a variety of manners such as having an opening in a wall of the contemplated analytical devices and/or using a port wherein the sample may be introduced via a pipette or syringe.

The plasma separation device is preferably configured to separate blood into a cell fraction and plasma fraction and capture a portion of the plasma fraction. A general configuration of the plasma separation device will include a first portion which is configured to separate blood into a cell fraction and plasma fraction and a second portion which is configured to capture a portion of the plasma fraction. The first portion may be a hydrophobic separation membrane or other such material which separates blood into a cell fraction and plasma fraction. For example, a Pall Vivid™ GX, glass fiber media, and fine fibrous media. Moreover, the first portion may comprise of fluidly separate areas wherein the plasma fraction is biased in one or multiple areas and the remaining fluid is biased in another direction. Furthermore, the first portion may be capable of further separating the remaining fluid into various areas within. In a further preferred embodiment, the second portion may be a hydrophilic membrane which has a void volume for the collection of a predetermined volume of plasma. For example, an Ahlstrom Cytosep® 1660 or polyurethane, TPU and cross-linked membranes. Additionally, the void volume may be uniform or may vary throughout the second portion so the void volume may control the flow of the plasma fraction. It can be appreciated that the second portion can be compressible which means that it can be of flexible, rigid, or a combination as long as it is capable of being compressed for the restriction of flow between the first and second portions. Finally, the second portion may extend from the plasma separation device into one or more compartments or conduits.

As described above the first and second portions can be fluidly coupled to allow flow of the plasma fraction between the first portion and the second portion. The flow of the plasma fraction between the first and second portion may be accomplished by a variety of manners. For example, an area of the first portion can be in direct contact with an area of the second portion wherein the contact between the first and second portion cause the flow of the plasma fraction, typically with capillary force. Alternatively, the first and second portion can be coupled by an intermediate membrane which makes contacts with an area of the first and second portion. Using an intermediate membrane allows for the possibility that a higher volume of plasma fraction may be captured. In addition, the intermediate membrane may further separate blood into a cell fraction and plasma fraction or capture the plasma fraction. Other possibilities for the intermediate membrane may comprise of other known techniques of separation, such as a filtering system with descending pore size using a combination of glass fiber membranes and cellulose membranes as described in U.S. Pat. No. 4,987,085 to Allen et al., or magnetic beads that are coupled to an affinity marker as described in U.S. Pat. No. 7,214,544 to Poirier et al., or antibodies that are coupled to the surfaces of paramagnetic beads U.S. Pat. No. 6,291,249 to Mahant et al. In further embodiments, at least one of the first and second portions comprises a dried and dissolvable indicator reagent to produce a visible indicator in the second portion when a satisfactory amount of the plasma fraction has been collected in the second portion. Additionally, other types of reagents may be applied such as for solvents, catalysts, buffers, auxiliaries and other types of reagents used for analyzing a sample.

Furthermore, it is contemplated that separation of the blood-containing fluid can be driven by capillary action. However, it should be appreciated that the blood-containing fluid may be driven in a variety of manners with similar results. For example, the blood-containing fluid may be driven by mechanical force wherein actuators compress a portion of the plasma separation device to drive the fluid through the device. Another example can be using a substance to create an affinity (e.g., hydrophilic interaction) with the plasma fraction wherein the plasma fraction is driven through the plasma separation device and captured and received by the second portion.

Analytical devices described herein may comprise of actuators which can generally function to isolate a portion of the plasma fraction by restricting the flow of the plasma fraction and subsequently compressing the isolated portion to cause the isolated portion to flow. Moreover, it may be possible that actuators may be used to introduce different reagents to the isolated portion by compressing adjacent chambers wherein the mixture in the isolated portion is then compressed into a chamber. It is generally preferred that a first actuator is configured as a knife edge. The knife edge can come in a plurality of forms such as a curved shape, a compound edge from multiple components, a series of pins, and a combination thereof, so long as the knife edge is capable of restricting the flow of the plasma fraction between the first and second portions. The width is preferably less than 5 mm, more preferably less than 3 mm. Regardless of shape and dimensions, it should be appreciated that suitable edges will be able to at least temporarily restrict the flow of the plasma fraction from the first portion to the second portion. In further embodiments, the knife edge may be locked by a locking mechanism. It is also contemplated that the knife edge could be part of the pouch or even snaps into place. If multiple edges are used, the edges may be individually controlled or controlled in common. With respect to a second actuator, the second actuator may comprise of some of the characteristics of the first actuator so long as flow is created of a metered volume of the plasma fraction when compressing the second area into at least one of the sample receiving compartment and a second compartment. Furthermore, it is contemplated that the second actuator can compress at least one of a portion of the metered volume and the entire metered volume. It may follow that if the second actuator may compress a portion of the metered volume, the second actuator may compress portions of the metered volumes into different compartments. Finally, it may be possible that contemplated analytical devices may use a single actuator. The single actuator can compress a first area to restrict the flow of the plasma fraction between the first and second portion and possibly compress a second area by rolling from the position of the first area onto a second area, thus causing flow of a metered volume of the plasma fraction.

It should be further appreciated that actuators of contemplated analytical devices may be made of a variety of materials. The actuators may be made of metals, polymers, and composites so long as the structure is stable enough to compress a first area to restrict flow and a second area to cause flow of a metered volume. Moreover, it may be possible that the actuators are automated and/or manual.

With respect to the metered volume of the plasma fraction, it is generally preferred that the metered volume can be determined by at least one actuator and/or a void volume in the second portion of the plasma separation device. The second portion may be manipulated in size and shape depending upon the volume of plasma that must be captured. As described above, the second portion may also be comprised of a plurality of materials and configurations which may affect the metered volume. It is further preferred that a flow of the metered volume is created by the compression of the second area which is isolated by the compression of the first actuator. Finally, it is contemplated that the metered volume can be determined by use of multiple and fluidly independent strips in the second portion which interact with the plasma separation device.

Contemplated analytical devices can comprise of a third compartment that includes a reagent which is fluidly coupled to the sample receiving compartment to allow flow of the reagent into the second portion. The reagents introduced may comprise of those discussed above. Moreover, the third compartment may be fluidly coupled where an actuator compresses an area of the third compartment and the reagent housed within flows out to the sample receiving compartment. Additionally, the second portion and the third compartment can be coupled by having multiple layers interconnected, having the second portion extend into the third compartment, and/or any other means that encourage the second portion and the third compartment to interact. The reagent can be introduced for the purposes of accelerating the separation of plasma fraction and cell fraction, indicating a sufficient amount of plasma fraction within the second portion and/or preparing a portion of the blood-containing fluid for an analytical test. Finally, it is possible that the reagent remains in the first portion of the plasma separation device and/or travels into the second portion of the plasma separation device.

Therefore, and viewed from a different perspective, a method is contemplated for manipulating a sample for a diagnostic test. Such method comprises a blood-containing fluid which makes contact with a plasma separation device that has a first portion and a second portion. The first portion then separates the blood-containing fluid into a cell fraction and a plasma fraction, and the second portion captures the plasma fraction. Thereafter, a first actuator fluidly isolates a portion of the plasma fraction within the second portion and a second actuator moves the isolated portion of the plasma fraction from the second portion. With respect to the same components, such as the plasma separation device, first portion, second portion, first actuator, second actuator, cell fraction, and plasma fraction, the properties previously described apply.

In especially preferred methods, contemplated analytical devices can comprise of a step for mixing reagents with the isolated plasma fraction in the second portion. As described above, the reagent can be introduced by actuators or other means and can perform a variety of functions. For example, the reagent can be stored in a compartment coupled to the second portion wherein an actuator compresses the compartment to release the reagent into the second portion. In further embodiments, reagents or combinations of reagents can be introduced to the isolated plasma fraction. Additionally, a plurality of actuators can segregate portions of the isolated plasma fraction wherein one region of the isolated plasma fraction is reacted with a reagent and moved, and then a second region of the isolated portion is reacted with a reagent and moved, and so on.

Therefore, a method of manipulating a sample for a diagnostic test is preferably contemplated where a capillary force in a plasma separation device separates a blood-containing fluid into a cell fraction and a plasma fraction. Thereafter, a compressible membrane receives and retains at least some of the plasma fraction. A first portion of the compressible membrane is then compressed wherein a portion of the plasma fraction is isolated within the compressible membrane. Finally, a second portion of the compressible membrane is compressed while maintaining compression of the first portion which thereby dispenses a predetermined volume of the plasma fraction from the compressible membrane. It is contemplated that the second portion which is compressed contains the isolated plasma fraction. With respect to the same components, such as plasma separation device, blood-containing fluid, first portion, second portion, plasma fraction, and predetermined volume of the plasma fraction, the same properties outlined above apply.

As noted above, the compressible membrane can be coupled to a hydrophobic separation membrane. Moreover, the compressive force can be applied to the first and second portion through a flexible wall of a container. Finally, it may be possible that a component in the plasma fraction may be reacted with a reagent while the plasma fraction is in the second portion.

In an exemplary embodiment, contemplated analytical devices comprise of a flexible test pouch with a multitude of chambers. These chambers may contain a variety of reagents, including magnetic beads, substrate, antibody solution, and wash buffer. In addition, there is a sample receiving compartment and a waste chamber. Coupled to the sample receiving compartment is a plasma separation device composed of a hydrophobic membrane and hydrophilic membrane. The two membranes are attached to each other in such a way as to facilitate the movement of plasma from the first portion which separates blood into cell fraction and a plasma fraction and the second portion which captures the plasma fraction. Moreover, a portion of the capture membrane may extend from the plasma separation device into a sample chamber in contemplated analytical devices. Finally, an analyzer comprising a series of actuators applies forces to various chambers of the pouch, thereby moving, mixing, and separating the sample with the reagents and a signal detector measures the signal generated by the chemical reaction (see U.S. Pat. No. 7,214,544 to Poirier et al. for an exemplary discussion on signal detection).

As used herein, the term "cell fraction" in conjunction with a plasma separation device refers to a fraction that is prepared from a blood-containing fluid and that has a higher cell count per volume than the blood-containing fluid from which it originated. Similarly, the term "plasma fraction" in conjunction with a plasma separation device refers to a fraction that is prepared from a blood-containing fluid and that has a lower cell count per volume than the blood containing fluid from which it originated (in both cases excluding a reduction in cell count per volume by dilution). For example, a plasma fraction will typically have a cell count of 100,000 nucleated cells or less per 0.1 milliliter, more typically 5,000 nucleated cells or less per 0.1 milliliter, and most typically 1,000 nucleated cells or less per 0.1 milliliters.

EXPERIMENTS

To gain a general understanding of an embodiment the following example and experiments are presented. In an exemplary embodiment, several drops of whole blood are placed in the sample receiving compartment. The amount of blood may be approximately 80 to 100 uL. In addition, several drops of a diluent or chase reagent may be added to the sample receiving compartment in order to speed the separation process. The blood is then absorbed onto the plasma separation membrane where the plasma flows through the first portion and is captured by the second portion until the second portion is saturated. For a blood sample of approximately 80 to 100 uL, the saturation volume can be approximately 20 uL. The first actuator applies a force against one end of the second portion to prevent any plasma from flowing back into the first portion wherein a portion of the plasma is isolated. Next, an actuator applies a force to an adjacent chamber containing a first reagent. This first reagent surrounds and interacts with the isolated portion of the second portion and the plasma fraction therein. After an incubation period, a second actuator applies a force to the isolated portion, resulting in a force which forces the mixture of the reagent and plasma fraction into another chamber. This process is repeated until the assay is completed.

Tests to determine the amount of sample that can be reliably extracted from the sample pad were performed and the results are described below. These tests are only intended to be illustrative of some of the principles set forth above, and are not intended to be read as limitations on the scope of the claimed subject matter.

Experiment Set 1

Figure 2:
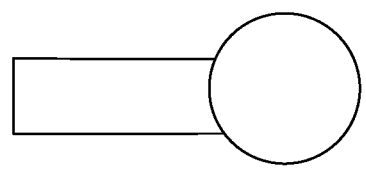
FIG. 2 is an exemplary illustration of the shape of a sample pad used in the some experiments discussed below.

In a first series of experiments, the sample volumes on the sample pads were determined by weighing the pads before and after sample introduction. The sample pads used were Ahlstrom CYTOSEP 1660 specialty paper and were cut to a specific size of 14 mm by 7 mm and shape as shown in FIG. 2. After sizing the sample pads, plasma was added to a blood separation device to determine the approximate capacity of the sample pad when cut to the above dimensions.

Table 1 depicts the measurements found when plasma was added to sample pad.

TABLE 1

|  | Weight 1 (mg) | Weight 2 (mg) | Weight 3 (mg) | Average (mg) |
| --- | --- | --- | --- | --- |
| Blank Sample Pad | 12.0 | 12.1 |  | 12.0 |
| Saturated Sample Pad | 28.2 | 33.4 | 30.3 | 30.6 |

Based on the figures in the table above, the net weight of the sample was 18.6 mg. The precision of the gravimetric measurements for the samples were thus calculated as having a mean of 18.6 mg, standard deviation of 2.62 mg, and a coefficient of variation of 14.1%.

Experiment Set 2

In a second series of experiments, a volume was transferred from the sample pad to a TSH immunoassay to determine extraction volume efficiency. This determination was performed by using: (1) sample volumes of 10 µL, 20 µL, and 30 µL directly pipetted into FastPack TSH assay pouches wherein the assay was conducted; and (2) pads containing sample that were sealed into the sample chambers of multiple FastPack TSH pouches wherein the assay was conducted. Six replicates using three different analyzers were used. Moreover, 20 µL of samples were pipetted onto each of 9 sample pads and sealed into the sample chambers of individual FastPack pouches. Based on the above, a TSH standard curve was developed using the sample volumes of 17.5 µL and 20 µL. The extracted volumes were then calculated based upon the chemiluminescent signal generated (RLUs or Relative Light Units). Thus, the average volume of sample extracted was determined to be 17.6 µL and the extracted volume efficiency based on the addition of a 20 µL sample to the pad was 87.8%.

Experimental Set 3

In a third series of experiments, the precision was determined by calculating the mean, standard deviation, and coefficient of variation of the sample pads in experimental set 2. However, note that in order to reduce the effects of reagent/assay imprecision on the extraction contribution of the variation, the samples used will have a target concentration of 20 IU/mL.

Table 2 depicts the precision of the sample volume extraction.

TABLE 2

|  | Test Samples | 17.5 uL Stds | 20.0 uL Stds |
|---|---|---|---|
| Mean (uL) | 17.6 | 17.5 | 20 |
| Standard Deviation (uL) | 0.54 | 0.45 | 0.27 |
| Coefficient of Variation | 3.06% | 2.56% | 1.33% |

Besides the numbers illustrated above, the chemistry only coefficient of variations as calculated from the standard replicates (no sample pad used) was determined to be 2.04%. Moreover, the total assay coefficient of variation for unknowns using the sample pad was 3.06%. Finally, the coefficient of variation of the extraction component (volume) was 2.28%.

Additionally, the precision was analyzed for analyte concentration in the sample. The findings are summarized in the table below.

Table 3 depicts the precision analyzed for analyte concentration in the sample.

TABLE 3

|  | Test Samples | 17.5 uL Stds | 20.0 uL Stds |
|---|---|---|---|
| Mean (uIU/mL) | 21.1 | 21.0 | 23.3 |
| Standard Deviation (uIU/mL) | 0.48 | 0.40 | 0.24 |
| Coefficient of Variation | 2.29% | 1.92% | 1.03% |

Moreover, the chemistry only coefficient of variation as calculated from the standard replicates (no sample pad used) was 1.54%. Further, the total assay coefficient of variation for unknowns using the sample pad was 2.29% and the coefficient of variation of the extraction component (TSH concentration) was 1.70%. Finally, the TSH recovery based on addition of a 20 uL sample to the pad was 90.5%.

In sum, the data summarizes that sufficient sample can be reliably extracted from the sample pad and presented to an immunoassay. Whatever added imprecision resulted from use of the sample pad was very small.

The following issued and published patents are hereby incorporated by reference: U.S. Pat. No. 6,291,249 to Mahant et al.; U.S. Pat. No. 6,426,230 to Feistel; U.S. Pat. No. 7,214,544 to Poirier et al.; U.S. Pat. No. 6,821,790 to Mahant et al.; U.S. Pat. No. 7,871,813 to Wyatt et al.; U.S. Pat. No. 6,300,138 to Gleason et al.; U.S. Pat. No. 7,754,499 to Poirier et al.; U.S. Pat. No. 7,629,165 to Wyatt et al.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An analytic device, comprising:
    a sample receiving compartment;
    a plasma separation device that is at least partially disposed in the sample receiving compartment and comprises (1) a first portion configured to separate blood into a cell fraction and a plasma fraction, and (2) a second portion, which is compressible and configured to capture at least a portion of the plasma fraction;
    wherein the analytic device comprises a flexible first area that, when compressed by a first actuator, compresses one a first part of the second portion and thereby restricts flow of the plasma fraction between the first and the second portion; and
    wherein the analytic device has a second area that, when compressed by a second actuator, compresses a second part of the second portion to dispenses a metered volume of the plasma fraction from the second part of the second portion into at least one of the sample receiving compartment and a second compartment.

2. The device of claim 1, wherein the first portion comprises a hydrophobic separation membrane.

3. The device of claim 1, wherein the second portion comprises a hydrophilic membrane having a void volume for collection of a predetermined volume of plasma.

4. The device of claim 1, wherein the first and second portions are fluidly coupled to each other to allow capillary flow of the plasma fraction from the first portion to the second portion.

5. The device of claim 1, wherein the first area is formed from a flexible wall of the analytic device.

6. The device of claim 1, wherein the first actuator is configured as a knife edge.

7. The device of claim 1, wherein the second area is formed from a flexible wall of the analytic device.

8. The device of claim 1, wherein the metered volume is determined by movement of the second actuator and/or a void volume in a membrane in the second portion of the plasma separation device.

9. The device of claim 1, further comprising a third compartment that includes a reagent and that is fluidly coupled to the sample receiving compartment to allow flow of the reagent into the second portion, or further comprising a dried and dissolvable indicator reagent in at least one of the first and second portion and present in an amount effective to produce a visible indicator in the second portion when a satisfactory amount of the plasma fraction has been collected in the second portion.

10. A method of manipulating a sample for a diagnostic test, comprising:
    contacting a plasma separation device with a blood-containing fluid, wherein the plasma separation device has a first portion and a second portion;
    using the first portion to separate the blood-containing fluid into a cell fraction and a plasma fraction, and using the second portion to capture the plasma fraction;
    using a first actuator to fluidly isolate a portion of the plasma fraction within the second portion by compressing a first part of the second portion; and
    using a second actuator to move the isolated portion of the plasma fraction from the second portion by compressing a second part of the second portion while the first actuator compresses the one part of the second portion.

11. The method of claim 10, wherein the plasma separation device is at least partially disposed within a container.

12. The method of claim 10, wherein separation of the blood-containing fluid is driven by capillary action.

13. The method of claim 10, wherein the first actuator has a knife edge that compresses the one part of the second portion of the plasma separation device.

14. The method of claim 10, wherein the first actuator snaps into place and compresses the one part of the second portion to restrict flow of the plasma fraction between the first and second portions.

15. The method of claim 10 further comprising a step of reacting a component in the plasma fraction with a reagent while the plasma fraction is in the second portion.

16. The method of claim 15 further comprising a step of moving the plasma fraction and the reagent from the second portion using the second actuator.

17. A method of manipulating a sample for a diagnostic test, comprising:
 using capillary force in a plasma separation device to separate a blood-containing fluid into a cell fraction and a plasma fraction;
 receiving and retaining at least some of the plasma fraction in a compressible membrane;
 compressing a first portion of the compressible membrane to thereby fluidly isolate a portion of the plasma fraction within a second portion of the compressible membrane, wherein the second portion of the compressible membrane provides a predetermined sample volume; and
 compressing the second portion of the compressible membrane while maintaining compression of the first portion to thereby dispense the predetermined volume of the plasma fraction from the second portion of the compressible membrane.

18. The method of claim 17, wherein the compressible membrane is coupled to a hydrophobic separation membrane.

19. The method of claim 17, wherein at least one of the steps of compressing the first and the second portion is performed through a flexible wall of a container.

20. The method of claim 17, further comprising a step of reacting a component in the plasma fraction with a reagent while the plasma fraction is in the second portion.

* * * * *